United States Patent [19]

Gruber et al.

[11] 4,260,809
[45] Apr. 7, 1981

[54] COPOLYMERIZABLE, ULTRAVIOLET LIGHT ABSORBER 4-ALKOXY-2'-ACRYLOXY BENZAZINES

[75] Inventors: Bruce A. Gruber, Worthington, Ohio; Donald H. Lorenz, Basking Ridge, N.J.

[73] Assignee: GAF Corporation, New York, N.Y.

[21] Appl. No.: 132,195

[22] Filed: Mar. 20, 1980

[51] Int. Cl.³ .............................................. C07C 69/54
[52] U.S. Cl. ............................. 560/138; 260/45.85 E; 560/221
[58] Field of Search ................................ 560/221, 138

[56] References Cited

U.S. PATENT DOCUMENTS 3,925,236  12/1975  Goldmacher et al. ................ 560/138

OTHER PUBLICATIONS

Hackh's Chemical Dictionary, Fourth Edition, p. 15, (1972).

Primary Examiner—Jane S. Myers
Attorney, Agent, or Firm—James Magee, Jr.; Walter Katz

[57] ABSTRACT

This invention relates to copolymerizable ultraviolet light absorber compounds having the formula

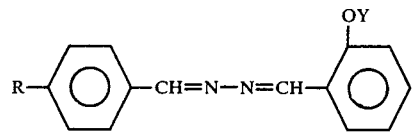

where R is alkyl $C_1$—$C_6$, substituted alkyl $C_1$—$C_6$ or alkoxy $C_1$—$C_6$; and Y is a copolymerizable radical selcted from acryloyl $C_3$—$C_{12}$, acryloxyalkyl $C_3$—$C_{12}$, acryloxyhydroxyalkyl $C_3$—$C_{12}$, and alkylacryloxyhydroxyalkyl $C_3$—$C_{12}$.

6 Claims, No Drawings

COPOLYMERIZABLE, ULTRAVIOLET LIGHT ABSORBER 4-ALKOXY-2'-ACRYLOXY BENZAZINES

BACKGROUND OF THE INVENTION

1. Field of the Invention

This invention relates to novel copolymerizable ultraviolet light absorber compounds, and, more particularly, to 4-alkoxy-2'-acryloxybenzazine compounds which are copolymerizable with vinyl monomers to provide polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,724. These ultraviolet absorbers are mechanically mixed with the plastic materials to prevent discoloration and degradation of the material. However, it has been observed that such absorbers sometimes fail or are locked out of the plastic under adverse weather conditions before the lifetime of the protected material. Also, it is not possible to use all of these ultraviolet absorbers with radiation curing of the plastic material. Another disadvantage of these ultraviolet absorbers is the high amount of absorber needed for protection of some materials.

Still another limitation on the use of prior art absorbers is that they provide little or no protection in the 330 to 400 nm region, which is a desirable region when the absorbers are used for skin and hair care products, such as suntan preparations and hair tinting compositions.

Accordingly, it is an object of the present invention to provide novel copolymerizable ultraviolet light absorber compounds which are substantially free of the disadvantages of the prior art.

A particular object of this invention is to provide novel compounds which can be copolymerized directly with monomers, such as plastic material, to provide more permanent ultraviolet light protection.

A specific object is to provide ultraviolet light absorber compounds containing a copolymerizable acryloyl group which exhibits absorption in the 330 to 400 nm region.

These and other objects and features of the invention will be made apparent from the following more particular description of the invention.

SUMMARY OF THE INVENTION

What is provided herein are improved, novel copolymerizable ultraviolet light absorber compounds of the formula:

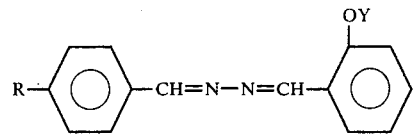

where
  R is alkyl $C_1$–$C_6$; substituted alkyl $C_1$–$C_6$ or alkoxy $C_1$–$C_6$; and
  Y is a copolymerizable radical selected from acryloyl $C_3$–$C_{12}$, alkylacryloyl $C_3$–$C_{12}$, acryloxyalkyl $C_3$–$C_{12}$, and alkylacryloxyhydroxyalkyl $C_3$–$C_{12}$.

In the best mode of the invention, R is methoxy and Y is acryloyl.

DETAILED DESCRIPTION OF THE INVENTION

The compounds of the invention contain ultraviolet light absorber and copolymerizable portions in the same molecule. These portions are effectively separated so that each can perform its own function without interference from the other. Therefore, the adsorber portion does not inhibit the copolymerization, and the ethylenic radical does not affect the light absorbing properties of the molecule.

The Y radical is copolymerizable with vinyl monomers so that the ultraviolet absorber becomes an integral part of the polymer. Suitable Y groups are derived from acryloyl, alkylacryloyl, acryloxyalkyl, acryloxyhydroxyalkyl and alkylacryloxyhydroxyalkyl, having from $C_3$–$C_{12}$ carbon atoms. The preferred groups are acryloyl, methacryloyl, acryloxyhydroxypropyl, and methacryloxyhydroxypropyl. The best mode is represented by acryloyl.

The novel compounds of the invention may be prepared from, e.g. 2-hydroxy-4'-methoxybenzazine, by reaction with an acryloyl halide.

The starting materials for the reaction are obtained by a two-step condensation of the commercially available substituted benzaldehydes with hydrazine. For example, p-methoxybenzaldehyde is condensed with hydrazine (1:1 molar ratio), followed by reaction with o-hydroxybenzaldehyde (1:1 molar ratio) (Step a below).

The novel compound of the inventions generally are yellow solids which are insoluble in water. The benzazine chromophore of the compounds herein has an ultraviolet absorbence peak at about 325 nm, but no visible absorbance with formylhydrazine in aqueous solution at reflux temperatures. The desired intermediate is obtained upon basification of the solution, giving a precipitate of the compound in yields of 60–70%.

The flow sheet below illustrates the reaction sequence for preparing the compounds of the invention.

Step (a)

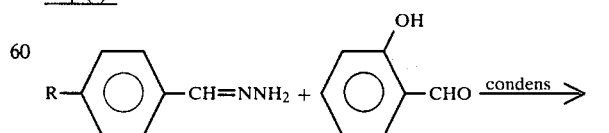

Step (b)

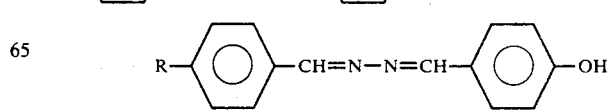

-continued

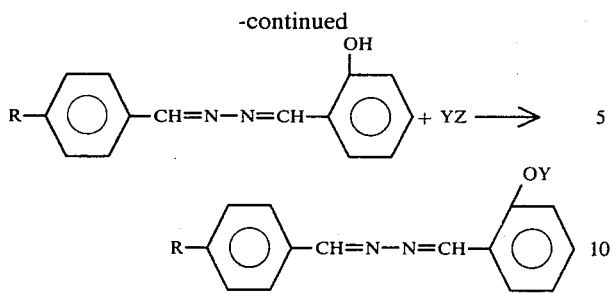

where Z is a halide and R and Y are as defined above.
Representative Y groups are —C—CH=CH₂(acryloyl), —C—C(CH₃)=CH₂(methacryloyl),
‖                      ‖
O                      O —CH₂CH(OH)CH₂OCCH=CH₂(3-acryloxy-2-hydroxypropyl),
            ‖
            O and —CH₂CH(OH)CH₂OCC(CH₃)=CH₂(3-methacryloxy-
                ‖
                O
2-hydroxypropyl).

In step (a), the hydrazone is dispersed in ethanol with sodium acetate. Then o-hydroxybenzaldehyde and acetic acid in ethanol are added with stirring until the azine separates. The product is filtered and the yield is nearly quantitative.

The esterification step (b) is carried out with a reactive acryloyl compound, such as an acryloyl halide, e.g. acryloyl chloride or acryloyl bromide, in aqueous base, such as a sodium hydroxide solution, at room temperature. Suitably the molar ratios of the reactants are controlled to provide at least 1:1 molar ratio of the acryloyl halide to the hydroxy intermediate. The product of the reaction precipitates, is filtered, and dried. The yield of the product in step (b) is about 80–90%.

The compounds of the invention may be copolymerized with monomers and oligomers by conventional free radical or with radiation curing, to provide useful polymeric coatings, or formulated into cosmetic preparations, such as skin and hair care products.

The following examples will describe the invention with more particularlty.

EXAMPLE 1

4-Methoxy-2'-Acryloxybenzazine

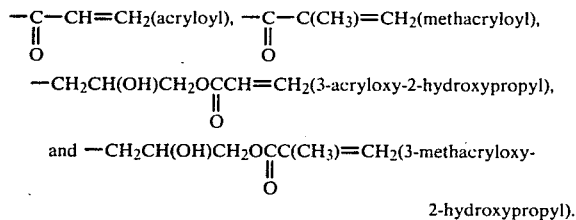

Step (a)

4-Methoxy-2'-Hydroxybenzazine

Into a flask equipped with a mechanical stirrer is charged 17.9 g of p-methoxyphenylhydrazone, 500 ml absolute ethanol and 12 g sodium acetate. To the rapidly stirred suspension then is added 20 ml absolute ethanol containing 12 g (0.1 mole) o-hydroxybenzaldehyde and 5 ml glacial acetic acid. The suspension is stirred for 1 hour, then filtered, giving 28 g (98%) of the product.

Step (b)

To a solution of 550 ml. of acetone-water (2:1) containing 0.79 g sodium hydroxide is added 5 g 4-methoxy-2'-hydroxybenzazine. After dissolving completely, the temperature is raised to 35°–40° C. and 1.78 g acryloyl chloride is added dropurse. The solution then is stirred for 1 hr., concentrated to ½ of its original volume and cooled. A precipate separates which is filtered and dried to provide yellow crystals, weighing 2.3 g (40%). The product is characterized by its nmr spectra. The UV absorption peak is at 325 nm and K is 130.4.

EXAMPLE 2

4-Methoxy-2'-Methacryloxybenzazine

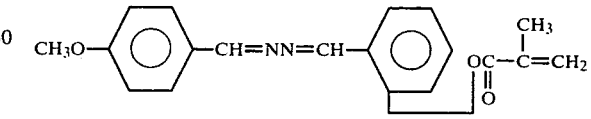

Using a molar equivalent amount of methacryloyl chloride in place of acryloyl chloride in Step (b) of Example 1, the desired methacrylate compound is obtained in comparable yield.

EXAMPLE 3

4-Methoxy-2'-(3-Acryloxy-2-Hydroxypropyl)oxybenzazine

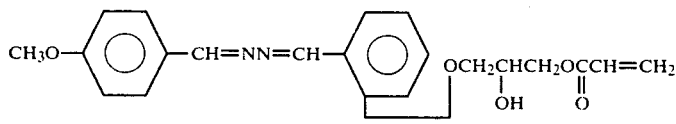

The procedure of Example 1 is followed except that the product of step (a), glycidyl acrylate in a molar amount equivalent to acryloyl chloride in Example 1, Step (b), and tetramethylammonium chloride are heated at 70°–90° C. for 5 hrs., and excess glycidal acrylate removed by vac distillation, to provide the desired compound.

EXAMPLE 4

4-Methoxy-2'-(3-Methacryloxy-2-Hydroxypropyl)oxybenzazine

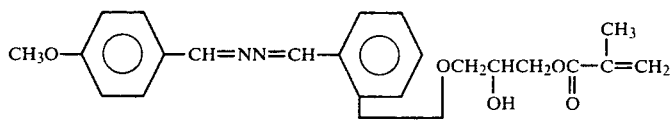

Using glycidyl methacrylate in place of glycidyl acrylate in Example 3 gives the corresponding methacrylate compound.

EXAMPLE 5

The monomer compound of Example 1 is copolymerized with another monomer by charging a flask with 150 ml ethanol, 1.5 g 4-methoxy-2'-acryloxybenzazine and 50 g vinyl pyrrolidone. The contents are heated to 75° C. under $N_2$ and polymerization is initiated with 0.2 g azobis-isobutyronitrile (AIBN). After 1.5 hrs., another 0.2 g AIBN is added and heating is continued for another 1.5 hrs. The solvent is concentrated and added to stirred ether. A white precipitate of the copolymer is obtained which is filtered and dried, giving 18 g (36%) of product. A 5% aqueous solution of the copolymer is filtered; the untraviolet spectra of the filtrate shows that the copolymer contains 5.8% of the absorber compound.

While certain preferred embodiments of the present invention have been illustrated by way of specific example it is to be understood that the present invention is in no way to be deemed as limited thereto but should be construed as broadly as all or any equivalents thereof.

What is claimed is:

1. Copolymerizable ultraviolet light absorber compounds having the formula:

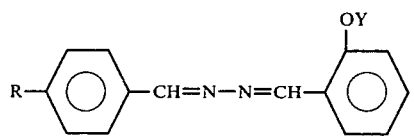

where
R is alkoxy $C_1$–$C_6$; and,
Y is a copolymerizable radical selected from acrylyl, methacrylyl, 3-acrylyloxy-2-hydroxypropyl or 3-methacrylyloxy-2-hydroxypropyl.

2. Compounds according to claim 1 wherein R is methoxy.

3. A compound according to claim 1 which is 4-methoxy-2'-acryloxybenzazine.

4. A compound according to claim 1 which is 4-methoxy-2'-methacrylyloxybenzazine.

5. A compound according to claim 1 which is 4-methoxy-2'-(3-acrylyloxy-2-hydroxypropyl)oxybenzazine.

6. A compound according to claim 1 which is 4-methoxy-2'-(3-methacrylyloxy-2-hydroxypropyl)oxybenzazine.

* * * * *